United States Patent
Niessen et al.

(10) Patent No.: US 7,193,120 B2
(45) Date of Patent: Mar. 20, 2007

(54) COLLOID-CATALYZED GAS TRANSFER IN SUPERCRITICAL PHASES

(75) Inventors: Heiko G. Niessen, Wesseling (DE); Klaus Woelk, Wachtberg (DE); Andreas Eichhorn, Alfter (DE); Joachim Bargon, Bonn (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 188 days.

(21) Appl. No.: 10/478,597

(22) PCT Filed: May 25, 2002

(86) PCT No.: PCT/EP02/05719

§ 371 (c)(1), (2), (4) Date: Apr. 9, 2004

(87) PCT Pub. No.: WO02/098925

PCT Pub. Date: Dec. 12, 2002

(65) Prior Publication Data

US 2004/0162377 A1 Aug. 19, 2004

(30) Foreign Application Priority Data

May 25, 2001 (DE) ................. 101 25 613

(51) Int. Cl.
C07C 5/02 (2006.01)

(52) U.S. Cl. .................. 585/263; 585/250; 585/275; 585/276; 525/338

(58) Field of Classification Search ............... 585/250, 585/263, 275, 276; 525/338
See application file for complete search history.

(56) References Cited

U.S. PATENT DOCUMENTS 5,238,607 A    8/1993  Herron et al.
6,002,047 A *  12/1999 Jansen et al. ............... 568/395
6,462,095 B1   10/2002 Boensel et al.
6,747,179 B1 *  6/2004 DeSimone et al. ......... 585/250

FOREIGN PATENT DOCUMENTS

| | | |
|---|---|---|
| DE | 195 06 113 | 8/1996 |
| DE | 197 45 904 | 4/1999 |
| DE | 199 13395 | 9/2000 |
| EP | 841 314 | 5/1998 |
| EP | 1 028 143 | 8/2000 |
| RU | 2 144 020 | 1/2000 |
| WO | 96/01304 | 1/1996 |
| WO | 01/14289 | 3/2001 |

OTHER PUBLICATIONS

Seregina et al., Chem. Mater. 9 (1997) 923-931.*
Polymer Bulletin 40, 173-180 (1998) Bronstein et al.
Chem.Mater.1997,9, 923-931, Seregina et al.
Derwent Abstract 2000-541726/49 of RU2144020.
RU 2144020 Abstract.
125:257959 Abstract of DE 19506113.
2001-160516/17 Derwent Abstract of DE 19913395.

\* cited by examiner

*Primary Examiner*—Roberto Rabago
(74) *Attorney, Agent, or Firm*—Novak Druce & Quigg LLP

(57) ABSTRACT

The invention relates to a process for hydrogen transfer to chemical compounds, wherein hydrogen transfer is carried out in a supercritical or subcritical phase using stabilized and dispersed metal particles. The invention further provides for the use of metal colloids stabilized by organic compounds or embedded in organic compounds as catalysts in a process for hydrogen transfer to chemical compounds in a supercritical or subcritical phase so as to avoid the formation of free-radical intermediates during hydrogen transfer.

13 Claims, No Drawings

COLLOID-CATALYZED GAS TRANSFER IN SUPERCRITICAL PHASES

The present invention relates to a process for hydrogen transfer to chemical compounds in the presence of stabilized metal colloids as catalysts, and to the use of stabilized metal colloids in a process for hydrogen transfer to chemical compounds.

Catalysis using metal colloids is usually carried out in conventional solvents.

DE-A 197 45 904 relates to metal colloid solutions which are stabilized by at least cation-exchange polymer. According to the description, the stabilized metal colloids are soluble in water or an organic solvent. The metal colloids disclosed in DE-A 197 45 904 are suitable as catalysts, in particular for fuel cells.

RU-C 214020 relates to a process for hydrogenating acetylenic alcohols to the corresponding ethylenic alcohols by means of hydrogen in the presence of micellar, palladium-containing catalysts. The catalysts are made up of Pd(0) which has been applied in the form of palladium acetate to a polystyrene-4-vinylpyridine block copolymer and subsequently reduced. In the final catalyst, the palladium nanoparticles obtained were applied to aluminum oxide.

DE-A 195 06 113 relates to liquid colloidal metal preparations containing micelles which comprise a block copolymer composed of at least one polymer block which is solvated by the solvent and a polymer block capable of binding the colloidal metal, in a liquid organic or inorganic solvent. None of the publications mentioned, which concern reactions catalyzed by metal colloids, disclose the use of supercritical fluids.

WO 01/14289 relates to a process for carrying out catalytic reactions in supercritical carbon dioxide, in which a fluid mixture comprising at least one reactant and carbon dioxide is brought into contact with a catalyst which is bound to a polymer and the reactant interacts with the catalyst to form a reaction product. The polymer used can be either soluble or insoluble in carbon dioxide. Suitable soluble polymers disclosed are polymers having $CO_2$-philic groups. As examples of $CO_2$-philic groups, mention is made of silicone-containing groups or polysiloxanes, halogen-containing (in particular fluorine-containing) groups or halogenated (in particular fluorinated) hydrocarbons and also branched polyalkylene oxides and fluorinated polyethers. The fluorine-containing unit is usually a "fluoropolymer". $CO_2$-phobic groups mentioned in WO01/14289 are, inter alia, aromatic polymers and oligomers made up of styrene, acrylate or vinylpyrrolidone monomers.

The processes for hydrogen transfer known from the prior art thus have the following disadvantages:

The products are difficult to separate off.
The catalyst is difficult to separate off.
Reaction rates are low.
Owing to the low solubility of the traditional catalyst systems, cationic homogeneous catalysis in a supercritical fluid is possible only when using fluorinated ligands or with the aid of fluorinated cosolvents.
The catalysts for cationic homogeneous catalysis in supercritical systems are expensive and, owing to the use of organic fluorine compounds, environmentally unfriendly.
Nonionic homogeneous catalysts display only a low reactivity.
The utilization of the catalytically active metal in heterogeneous catalysis is low.
The dead volume occupied by support material in heterogeneous catalysis is undesirable.
Products always contain traces of solvents. The engineering outlay for product purification, especially in the field of pharmaceuticals and foodstuffs, is high.
Diffusion limitation in reactions with gases in two-phase systems is a problem.
Reaction rates in supercritical fluids in particular are very low.

It is an object of the present invention to provide a process for hydrogen transfer to chemical compounds, which gives a high catalyst utilization and short reaction times, i.e. high conversion rates. Furthermore, a high reactivity of the catalyst used should be achieved under mild reaction conditions and with little by-product formation.

We have found that this object is achieved by a process for hydrogen transfer to chemical compounds, wherein hydrogen transfer is carried out in a supercritical or subcritical phase using stabilized and dispersed metal particles. The metal particles are preferably used in the form of metal clusters or particles in the colloidal size range.

Metal colloids are systems in which metal particles having a diameter in the range from 1 nm to 1 µm are present. The extremely finely divided metal itself is referred to as colloidal metal.

For the purposes of the present invention, metal clusters are metal particles which consist of a small number of metal atoms, from a few to a few thousand metal atoms, and are at the lower end of the size scale for colloidal metal (diameter of the metal particles in metal colloids: from 1 nm to 1 µm).

A preferred embodiment of the present invention pertains to a process for hydrogen transfer to chemical compounds in which the chemical compounds are reacted in the presence of catalysts comprising dispersed metal colloids stabilized by organic compounds or embedded in organic compounds.

In the process of the present invention, the reaction is then carried out in a supercritical or subcritical phase.

The generally well-known terms "supercritical" and "subcritical" (equivalent to "near-critical") are explained in, for example, the article "Interaction of Density, Viscosity and Interfacial Tension in Countercurrent Extraction with Near-Critical Fluids" in "High Pressure Chemical Engineering", pages 191 to 197, Ed. Ph. Rudolf von Rohr and Ch. Trepp, Elsevier Science B.V. 1996 and the literature cited therein.

The process of the present invention gives high reaction rates and thus has a high efficiency. Owing to the use of a supercritical solvent, no possibly toxic solvent residues remain the product, and product and catalyst can be separated off easily. The gaseous reactants display a maximum activity. The process of the present invention allows the advantages of heterogeneous catalysis (e.g. ease of separating off the catalyst) to be combined with those of homogeneous catalysis (e.g. catalyst utilization, selectivity).

Thus, the process of the present invention has the following advantages:

No toxic solvent residues in the product.
High efficiency.
Catalyst and product are easy to separate off.
Reaction rates found are superior to all those known hitherto.
Inexpensive, industrially available catalysts.
Reduced environmental pollution.
Low energy consumption as a result of mild reaction conditions.
Maximum activity of gaseous reactants.

Advantages of heterogeneous catalysis (ease of separating off the catalyst, etc.) and of homogeneous catalysis (catalyst utilization, selectivity, etc.) can be combined in supercritical systems.

As a result of the use according to the present invention of supercritical solvents, the hydrogen concentration in the solvent can be chosen virtually freely and is no longer a constraining factor in the reaction as is the case in liquid solvents, in which the solubility of hydrogen is low. The word supercritical refers to the state of the solvent (fluid) used. For example, carbon dioxide is in the supercritical state when the temperature is above 31.1° C. and at the same time the pressure is above 73.8 bar. Supercritical fluids display both liquid-like and gas-like properties, e.g. a liquid-like density and a gas-like viscosity. The diffusion rate in supercritical fluids is between the values for gases and liquids. Owing to increased mass transfer, gas-like properties are advantageous in reaction chemistry.

A particularly important property of supercritical fluids is that they are completely miscible with any type of gases, including hydrogen gas. This means that when the solvent is in the supercritical state, the hydrogen gas used for the reduction can be mixed with the solvent in a simple fashion.

When carrying out the process of the present invention, the choice of a suitable solvent depends on the type of hydrogen transfer reaction and on the starting materials used. Suitable solvents are, in particular, aromatic and aliphatic hydrocarbons such as benzene, toluene, ethane, propane or butane; carbon dioxide; alcohols such as methanol or ethanol; and mixtures thereof. Preference is given to using carbon dioxide and low molecular weight hydrocarbons such as ethane or propane. The supercritical or subcritical phase very particularly preferably comprises carbon dioxide. Carbon dioxide is environmentally friendly, nontoxic, nonflammable, inexpensive, noncorrosive and readily available. In the process of the present invention for hydrogen transfer, it can function simultaneously as solvent and protective gas.

The behavior of supercritical solvents can be modified by addition of a modifier, e.g. short-chain alcohols or esters.

The preparation of metal colloids has been known for a long time. The usual method is to reduce metal salts in solution to the metal in the presence of stabilizers (cf., for example, G. Schmid, VCH-Verlag 1994, Clusters and Colloids). The stabilizers are substances which are able to form coordinate bonds to the metal and thus protect it against agglomeration. In the process of the present invention, organic compounds are used as stabilizers. Suitable organic compounds are compounds capable of coordination (ligands) or polymers. Preferred organic compounds are, according to the present patent application, polymers.

The metal colloids stabilized by organic compounds or embedded in organic compounds will hereinafter be referred to as stabilized metal colloids. The stabilized metal colloids are preferably metal colloids embedded in organic compounds.

The stabilized metal colloids are preferably dispersible in the supercritical phase. It is known that the solubility of polymers in a supercritical phase, in particular in supercritical carbon dioxide, is moderate to poor. According to WO 01/14289, polymers containing $CO_2$-philic groups are soluble in carbon dioxide. As $CO_2$-philic groups, mention may be made of silicone-containing groups or polysiloxanes, halogen-containing (in particular fluorine-containing) groups or halogenated (in particular fluorinated) hydrocarbons and also branched polyalkylene oxide and fluorinated polyethers. It has surprisingly been found that the use of block copolymers as stabilizers, preferably block copolymers in which at least two polymer blocks are selected from the group consisting of polystyrene, polyalkylstyrene, polyisoprene, polymethyl (meth)acrylate and polybutadiene, poly-4-vinylpyridine, poly-2-vinylpyridine, polyethylene glycol, polyethylene oxide, poly(meth)acrylic acid, polyhydroxyethyl methacrylate, polyvinyl alcohol, polydimethylsiloxane, poly-2-dimethylaminoethyl (meth)acrylate and polyethylethylene, give catalysts which are colloidally dispersed in the supercritical phase, in particular in supercritical carbon dioxide. Particularly preferred stabilizers are block copolymers selected from the group consisting of polystyrene-poly-4-vinylpyridine, polystyrene-poly-2-vinylpyridine, polystyrene-poly(meth)acrylic acid, polystyrene-polyethylene glycol, polystyrene-polyethylene oxide, polystyrene-polyhydroxyethyl methacrylate, polystyrene-polyvinyl alcohol, polydimethylsiloxane-polyethylene oxide, poly-2-dimethylaminoethyl methacrylate-polymethyl methacrylate and polyethylene oxide-polyethylethylene. In these, polymethyl methacrylate can be used in place of polystyrene. Very particular preference is given to using polystyrene-poly-4-vinylpyridine block copolymers as stabilizers. The use of polymers mentioned in WO 01/14289, which are expensive because of the $CO_2$-philic groups mentioned in WO 01/14289, is not necessary.

The preparation of the block copolymers which are preferably used according to the present invention is known to those skilled in the art. They can be obtained, for example, by anionic polymerization of the corresponding monomers (M. Antonietti, Chem. Mater. 1997, No. 9, 923–931). The preparation of the particularly preferred polystyrene-poly-4-vinylpyridine block copolymers is carried out by a method disclosed in Bronstein et al., J. Catal. 196, 302 to 312 (2000).

In a preferred embodiment, the metal colloids are embedded in these polymers, preferably in the block copolymers described. Such stabilized metal colloids are obtained, for example, by the method of M. Antonietti, Chem. Mater. 1997, No. 9, 923–931.

For the purposes of the present patent application, metal colloids are metals, metal alloys or unalloyed metal combinations. These preferably consist of one or more metals selected from the group consisting of nickel, cobalt, palladium, platinum, gold, silver, copper, rhodium, ruthenium and iridium; particular preference is given to using one or more metals selected from the group consisting of palladium, gold, platinum, rhodium and ruthenium.

The metal colloids used according to the present invention very particularly preferably comprise a core of a metal selected from among the abovementioned metals, in particular gold, which is surrounded by a layer of a further metal which is selected from among the abovementioned metals but is different from the metal of the core, preferably palladium. The preparation of metal colloids made up of a core and a shell is described, for example, in G. Schmid, VCH-Verlag 1994, Clusters and Colloids and by Bronstein et al., J. Catal. 2000, vol. 196, p. 302–314.

A cosolvent can, if desired, be used to stabilize and disperse the metal particles. Preference is given to a cosolvent selected from the group consisting of toluene, o-, m-, p-xylene, α,α,α-trifluorotoluene, benzene, ethylbenzene, cyclohexane, hexane, pentane and partially fluorinated alcohols.

The hydrogen transfer reaction is preferably a reaction selected from the group consisting of hydrogenation, hydroformylation, hydrogenolysis, hydrocarboxylation and hydrosilylation. Particular preference is given to carrying out a hydrogenation or hydroformylation, very particularly preferably a hydrogenation.

The reagents with which the chemical compounds are reacted in a supercritical or subcritical phase in the presence of stabilized metal colloids as catalysts depend on the particular hydrogen transfer reaction and correspond to the reagents used in the corresponding processes known from the prior art.

The chemical compounds which are reacted in the process of the present invention are likewise dependent on the particular hydrogen transfer reaction and correspond to the chemical compounds used in the corresponding processes known from the prior art.

If the hydrogen transfer reaction is a preferred hydroformylation, hydrogen and carbon monoxide are used as reagents. The process of the present invention can be applied to all customary hydroformylations of chemical compounds. The chemical compounds used in the hydroformylation carried out according to the process of the present invention are preferably $C_2$ to $C_{20}$-olefins or alkynes.

In the particularly preferred hydrogenation reaction, the chemical compounds are reacted with hydrogen as reagent. The process of the present invention can be applied to all customary hydrogenations of chemical compounds. Preferred chemical compounds used in the hydrogenation carried out according to the present invention are selected from the group consisting of alkynes; alkynols; alkenes; in particular unsaturated fatty acids; nitro compounds; carboxylic acids, in particular fatty acids; carbonyl compounds and aromatic compounds.

Particularly preferred chemical compounds are alkynes and alkynols, very particularly preferably 1-hexyne, 3-methylpent-1-yn-3-ol, 3-phenylpropyne, 3,3-dimethylbutyne and phenylethyne.

The hydrogenation reactions which can be carried out using the process of the present invention can be unselective (i.e. complete) or selective hydrogenation. An example of a selective hydrogenation is the hydrogenation of alkynes to alkenes.

The process can in principle be carried out at any pressure/temperature combinations as long as it is ensured that a supercritical or subcritical phase is present. The precise pressure and temperature values are dependent on the particular hydrogen transfer reaction and the solvent used.

If the process is carried out in carbon dioxide, it is generally carried out at from 32 to 250° C., preferably from 40 to 100° C., particularly preferably 50° C., and from 74 to 350 bar, preferably from 100 to 200 bar, particularly preferably 150 bar, of carbon dioxide pressure (plus the pressure caused by the partial pressure of any gas used as reagent (e.g. hydrogenation: $H_2$; hydroformylation: CO and $H_2$)). The supercritical or subcritical phase is usually produced by the fluid used as solvent, preferably carbon dioxide, being compressed to the pressure mentioned in a reactor at the temperature mentioned. The addition of the chemical compounds, the catalysts and the reagent used as a function of the hydrogen transfer reaction and also, if desired, further components can be carried out before or after compression. Preference is given to the chemical compound, the catalyst, the reagent used as a function of the hydrogen transfer reaction and any further components being added to the fluid used as solvent first and the mixture then being compressed to the temperature mentioned and the pressure mentioned to produce the supercritical or subcritical phase.

If a particularly preferred hydrogenation is carried out, preference is given to introducing hydrogen in such an amount that a hydrogen partial pressure of generally from 1 to 100 bar, preferably from 2 to 50 bar, particularly preferably from 2 to 15 bar (pressure increase above the previously set internal pressure in the reactor), is established.

The amount of stabilized metal colloid used as catalyst is dependent on the hydrogen transfer reaction carried out. In the particularly preferred hydrogenation, the amount is generally from 0.01 to 5% by weight, preferably from 0.02 to 2% by weight, particularly preferably from 0.1 to 1% by weight, based on the chemical compound used.

The reaction time is likewise dependent on the hydrogen transfer reaction carried out and on the chemical compounds used. The reaction time is usually from 1 minute to 1 hour, preferably from 1 minute to 10 minutes.

The conversion rates achieved by means of the process of the present invention are significantly higher than the conversions achieved in the liquid phase. In the case of the particularly preferred hydrogenation, conversion rates are generally from 30,000 $h^{-1}$ to 8,000,000 $h^{-1}$, preferably from 100,000 $h^{-1}$ to 4,000,000 $h^{-1}$, particularly preferably from 500,000 $h^{-1}$ to 2,000,000 $h^{-1}$.

The process of the present invention can be carried out continuously, semi-continuously or batchwise, with preference being given to a continuous process.

The stabilized metal colloids used as catalysts according to the present invention can be recovered after the reaction and reused. Unreacted chemical compounds can likewise be recovered and reused.

In a preferred embodiment of the process of the present invention, a supercritical phase is produced by compressing the solvent so that it is present in a supercritical or subcritical state. This is followed, in the case of a particularly preferred hydrogenation, by introduction of hydrogen. The chemical compound to be hydrogenated and the stabilized metal colloid used as catalyst according to the present invention are subsequently added to the mixture. After the reaction, the components can be separated, for example, by filtration, ultrafiltration, distillation or sedimentation.

The process of the present invention can be carried out in all reactors customarily used for reactions in a supercritical or subcritical phase, e.g. stirred vessels or bubble columns.

The reactivity and selectivity of product formation can be controlled by variation of the reaction conditions, the metals, metal alloys or unalloyed metal combinations used, the stabilizers (preferably polymers) used for stabilizing the metal colloids, if desired addition of further substances as a function of the respective hydrogen transfer reaction, if desired by means of upstream reactions or by means of physical effects, with the variation preferably being carried out within the abovementioned ranges.

In particular, the use of stabilized metal colloids as catalysts in the process of the present invention results in a simultaneous, i.e. pairwise, transfer of the two hydrogen atoms of a hydrogen molecule occurring, which is typical of a homogeneous hydrogenation. The pairwise transfer of the hydrogen atoms avoids free-radical intermediates in the hydrogen transfer. The avoidance of free-radical intermediates avoids the formation of by-products which could be formed from such free-radical intermediates.

The present invention therefore further provides for the use of metal colloids stabilized by organic compounds or embedded in organic compounds as catalysts in a process for hydrogen transfer to chemical compounds in a supercritical or subcritical phase so as to avoid the formation of free-radical intermediates during hydrogen transfer.

In this way, the formation of by-products due to secondary reactions of free-radical intermediates usually formed is reduced.

Suitable organic compounds, metal colloids, processes for hydrogen transfer and supercritical solvents have been mentioned above.

The following example illustrates the invention.

EXAMPLE

Substrates and catalyst are placed in a suitable reactor or autoclave, in this case a high-pressure NMR sample head. Mixed transition metal colloids comprising a gold core surrounded by a layer of palladium are employed as catalysts. The representative colloids used here are stabilized by means of polystyrene-poly-4-vinylpyridine block copolymers (Bronstein, et al. J. Catal. 196, 302–312 (2000)).

As characteristic substrates, 1-hexyne, 3-methylpent-1-yn-3-ol, 3-phenylpropyne, 3,3-dimethylbutyne and phenylethyne are used as alternatives. To produce a supercritical solution, carbon dioxide at 50° C. is compressed in the reactor to a pressure of 150 bar. Hydrogen is subsequently introduced into the reactor by means of a piston pump (ISCO 100 DM, Lincoln, NE., USA). In separate experiments, each of the substrates indicated is hydrogenated at a constant additional pressure of hydrogen (15 bar pressure increase above the previously set internal pressure in the reactor of 150 bar of $CO_2$). The course of the respective reaction is monitored in-situ by means of NMR measurements. Evaluation of the signals which change during the course of the reaction, e.g. the alkyne hydrogen signal, enables the progress of the respective reaction to be determined. In the case of all the substrates used, the reaction rates determined are significantly higher than those obtained in organic solvents. To determine the pressure dependence of the reaction under examination, additional hydrogenations of both phenylethyne and 3-methylpent-1-yn-3-ol are carried out at 2, 4, 8, 10 and 15 bar. Over this pressure range (i.e. 2–15 bar additional hydrogen pressure), an increase in the conversion rates with increasing hydrogen pressure by a factor of 15 for phenylethyne and a factor of 20 for 3-methylpent-1-yn-3-ol is observed.

At a $CO_2$ pressure of 150 bar, an $H_2$ pressure (on top of the initially charged $CO_2$) of 15 bar and a substrate/catalyst ratio of about 6,500 and a temperature of 50° C., the following conversions (turnover frequencies (TOFs)) are obtained:

| | |
|---|---|
| 1-hexyne: | 1,180,000 $h^{-1}$ |
| phenylethyne: | 500,400 $h^{-1}$ |
| 3-hydroxy-3-methyl-1-pentyne: | 432,100 $h^{-1}$ |
| 1-phenyl-3-propyne: | 236,200 $h^{-1}$ |
| 3,3-dimethyl-1-butyne: | 104,700 $h^{-1}$ |

For comparison, a maximum conversion rate of about 30,000 $h^{-1}$ is obtained in hexane.

We claim:

1. A process for hydrogen transfer to chemical compounds in which the chemical compounds are reacted in the presence of catalysts comprising dispersed metal colloids in the form of at least one of metals, metal alloys and unalloyed metal combinations stabilized against agglomerization by block copolymers or embedded in block copolymers, wherein the reaction is carried out in a supercritical or near-critical phase.

2. A process as claimed in claim 1, wherein the block copolymers are selected from the group consisting of polystyrene-poly-4-vinylpyridine, polystyrene-poly-2-vinylpyridine, polystyrene-poly(meth)acrylic acid, polystyrene-polyethylene glycol, polystyrene-polyethylene oxide, polystyrene-polyhydroxyethyl methacrylate, polystyrene-polyvinyl alcohol, polydimethylsiloxane-polyethylene oxide, poly-2-dimethylaminoethyl methacrylate-polymethyl methacrylate and polyethylene oxide-polyethylethylene.

3. A process as claimed in claim 2, wherein the block copolymers used are polystyrene-poly-4-vinylpyridine block copolymers.

4. A process as claimed in claim 1, wherein the metal colloids comprise metals, metal alloys or unalloyed metal combinations consisting of one or more metals selected from the group consisting of nickel, cobalt, palladium, platinum, gold, silver, copper, rhodium, ruthenium and iridium.

5. A process as claimed in claim 4, wherein the metal colloids comprise a gold core surrounded by a layer of palladium.

6. A process as claimed in claim 1, wherein the supercritical phase comprises supercritical carbon dioxide.

7. A process as claimed in claim 1, wherein the hydrogen transfer is a reaction selected from the group consisting of hydrogenation, hydroformylation hydrogenolysis, hydrocarboxylation and hydrosilylation.

8. A process as claimed in claim 7, wherein the hydrogen transfer is a hydrogenation.

9. A process as claimed in claim 8, wherein the hydrogenation is carried out at a hydrogen partial pressure of from 2 to 15 bar.

10. A process for hydrogen transfer to chemical compounds in which the chemical compounds are reacted in the presence of catalysts comprising dispersed metal colloids in the form of at least one of metals, metal alloys and unalloyed metal combinations and block copolymers, wherein the block copolymers form coordinate bonds to the metal thereby protecting against agglomeration and wherein the reaction is carried out in a supercritical or near-critical phase.

11. A process as claimed in claim 10, wherein the reaction is carried out in a supercritical phase.

12. A process for hydrogen transfer to chemical compounds in which the chemical compounds are reacted in the presence of catalysts comprising dispersed metal colloids in the form of at least one of metals, metal alloys and unalloyed metal combinations stabilized against agglomerization by block coplymers or embedded in block coplymers, wherein the reaction is carried out in a supercritical phase.

13. A process for hydrogen transfer to chemical compounds in which the chemical compounds are reacted in the presence of catalysts comprising dispersed metal colloids in the form of at least one of metals, metal alloys and unalloyed metal combinations stabilized against agglomerization by block coplymers or embedded in block coplymers, wherein the reaction is carried out in a near-critical phase.

* * * * *